Figure 1:
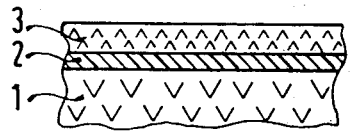

United States Patent [19]

Friese

[11] 4,354,912

[45] Oct. 19, 1982

[54] SOLID ELECTROCHEMICAL SENSOR

[75] Inventor: Karl-Hermann Friese, Leonberg, Fed. Rep. of Germany

[73] Assignee: Robert Bosch GmbH, Stuttgart, Fed. Rep. of Germany

[21] Appl. No.: 113,407

[22] Filed: Jan. 18, 1980

[30] Foreign Application Priority Data

Feb. 3, 1979 [DE] Fed. Rep. of Germany ....... 2904069

[51] Int. Cl.$^3$ .......................................... G01N 27/58
[52] U.S. Cl. ................................................ 204/195 S
[58] Field of Search .............. 204/15, 195 S; 123/489; 60/276

[56] References Cited

U.S. PATENT DOCUMENTS

| | | | |
|---|---|---|---|
| 3,300,344 | 1/1967 | Bray et al. | 429/33 |
| 3,359,188 | 12/1967 | Fischer | 204/1 T |
| 3,578,578 | 5/1971 | von Krusenstierna | 204/195 S |
| 3,776,831 | 12/1973 | Roy et al. | 204/195 S |
| 3,843,400 | 10/1974 | Radford et al. | 429/152 |
| 3,989,614 | 11/1976 | Tien | 204/195 S |
| 4,040,929 | 8/1977 | Bauer et al. | 204/195 S |
| 4,107,018 | 8/1978 | Bode et al. | |
| 4,126,532 | 11/1978 | Takao et al. | 204/195 S |
| 4,170,530 | 10/1979 | Watanabe et al. | 204/195 S |
| 4,257,863 | 3/1981 | Hoffman | 204/195 S |
| 4,265,724 | 5/1981 | Haecker et al. | 204/195 S |

*Primary Examiner*—G. L. Kaplan
*Attorney, Agent, or Firm*—Frishauf, Holtz, Goodman & Woodward

[57] ABSTRACT

To improve current loading of the electrodes and thus improve the start-up operation of an electrochemical system which includes a solid electrolyte body, particularly at temperatures in the order of about 300° C., the solid electrolyte body and the electrode layer thereover has an intermediate coating of fully stabilized zirconium dioxide applied; for example partially stabilized zirconium dioxide is fully stabilized in its surface region by yttrium or ytterbium oxide. This intermediate layer, while improving the current carrying capability of electrodes applied thereover, additionally prevents the occurrence of damage to the microstructure of partially stabilized solid electrolyte ceramic, particularly under changeable temperature loading, so that, if the solid electrolyte body essentially entirely consists of partially stabilized ceramic, the additional fully stabilized coating or surface zone can also be provided where the solid electrolyte body does not carry an electrode layer. The fully stabilized coating or layer - which may be a surface zone of the partially stabilized body - can be obtained by coating the partially stabilized body with a stabilization oxide which, in a heat treatment, is then diffused into the surface zone; or an aqueous suspension of about 92 mol-% $ZrO_2$ and 8 mol-% $Y_2O_3$ or 8 mol-% $Yb_2O_3$ can be applied, by spraying, dipping, or the like; up to 3% (by weight) of sinter-active $Al_2O_3$ is preferably added in order to improve sintering activity of the layer, over which, where desired, an electrode layer or a composite cermet electrode layer can be applied.

15 Claims, 2 Drawing Figures

SOLID ELECTROCHEMICAL SENSOR

The present invention relates to a solid electrolyte body to be used as an electrochemical sensor and which, basically, is a zirconium dioxide ceramic body.

BACKGROUND AND PRIOR ART

Solid electrolyte bodies in which an electrode layer is applied thereto are frequently used as electrochemical sensors. One such application is to sense the composition of exhaust gases from internal combustion engines, typically automotive-type internal combustion engines, by determining if the exhaust gases are reducing or oxidizing. Sensors of this type, also known as lambda sensors, carry an electrode layer on at least part of their surface. It has been customary to apply the electrode layer on the presintered solid electrolyte body and then sintering the electrode layer on the body. The electrode layer, which is exposed to the exhaust gases and possibly uncovered solid electrolyte body surface, can be covered with a porous ceramic cover layer which, after its application, is again sintered. Another method of application of such a porous protective layer is by plasma-spraying technology or flame-spraying technology. The electrodes, which are applied to a surface which is exposed usually to ambient air and which serves as a comparison electrode, customarily are not supplied with such a cover layer. Sensors which are formed as tubes which are closed at the end exposed to the gases usually carry the reference or comparison electrodes at the interior of the tube; the interior of the tube is in communication with ambient air through suitable openings in the socket or housing for the solid electrolyte body.

The electrode need not be a single layer; rather, it has been proposed already to use a system comprising a plurality of layers as the electrode, in which the layer which is closest to the solid electrolyte body itself forms the actual electrode connection. Such a layer system can have good adhesion on the body. In one method, the layer system is applied to the electrode body before sintering thereof, or before an intensive heat treatment; sinter processes in the electrode layer are then caused to occur. If a porous cover layer made of a ceramic material is already applied thereto, and this composite system is jointly sintered on the solid electrolyte body, the adhesion thereof on the solid electrolyte body, and hence of the electrode layer, will be excellent.

It has been found that sensors, and particularly those sensors which carry only a single or simple electrode layer, cannot be sufficiently loaded with electrical current. This is particularly apparent in the inner electrodes of such tubular sensors. Electrical loading capacity of the electrodes is important when the cells are cold, that is, upon starting of the engine with which the cells are associated, and hence upon starting of the sensing cycles of the sensors. The electrodes additionally can be subjected to a high electrode polarization, especially at lower temperatures, that is, at temperatures substantially below the operating temperature. Compensation for the difference in response characteristics can be obtained electronically, at the expense, however, of complex circuits.

THE INVENTION

It is an object to construct a solid electrolyte body, particularly suitable for an electrochemical sensor which is operational already at temperatures as low as 300° C., and which has higher electrode loading than heretofore possible, so that the sensor can be used in combination with an evaluation circuit without requiring extensive low-temperature compensation circuitry.

Briefly, in accordance with the invention, an intermediate layer is applied between the solid electrolyte body and the electrode layer or electrode layer system, the intermediate layer being characterized by having a higher specific ion conductivity than the solid electrolyte body. In one preferred arrangement, the solid electrolyte body is a partially stabilized zirconium dioxide ceramic; the intermediate layer is a fully stabilized zirconium dioxide ceramic with stabilization components which include $Y_2O_3$ and/or $Yb_2O_3$ and/or $Sc_2O_3$ and/or oxides of other heavy rare earth.

In partially stabilized solid electrolyte ceramic bodies, the intermediate layer also prevents the occurrence of disturbances of the structure or microstructure of the solid electrolyte body due to thermal loading, and particularly upon variable thermal loading or changes in thermal loading; the intermediate layer can also be applied on partially stabilized ceramic in those locations where the solid electrolyte body does not carry an electrode cover.

In accordance with a feature of the invention, a method of applying the intermediate layer on the solid electrolyte body comprises applying a suspension of fully stabilized zirconium dioxide powder on the body, which is presintered, and then applying the electrode layer or electrode layer system on this intermediate layer and finally sintering the entire assembly. In accordance with another feature of the invention, the partially stabilized presintered solid electrolyte body has a thin layer of a stabilization oxide applied thereon, which is then presintered, and thereafter the electrode layer or electrode layer system is applied thereover, and the solid electrolyte with the layers thus applied is then finally sintered.

It has been found that the $O^{2-}$ ion conductivity of the usual solid electrolyte material drops sharply as the utilization temperature decreases, for example decreases to below 300° C., thus causing the interior or inherent resistance of the sensor to rise correspondingly. Consequently, sensors as previously proposed could operate satisfactorily only at higher temperatures, particularly when the higher electrode polarization was also considered. The solid electrolyte body, with the electrode layer applied over an intermediate layer, has the particular advantage that the electrical loading capacity is high, while further exhibiting excellent adhesion of the layer system on the solid electrolyte body itself. The solid electrolyte bodies, when used as exhaust gas sensors, usually are not completely made of stabilized cubic $ZrO_2$, due to the high requirements placed on mechanical and thermal characteristics, especially when used as exhaust gas sensors in mobile automotive-type engine exhaust systems. The ion conductivity, therefore, is decreased since the ceramic is diluted, as customary, with non-ion conductive components such as baddeleyite, a monoclinic modification of zirconium dioxide, or $\alpha$-$Al_2O_3$. A stabilizer oxide such as pure $Yb_2O_3$ which, by itself, would be more desirable as a stabilizer for the ceramic body cannot be used due to its high cost.

DRAWING

Figure 2:
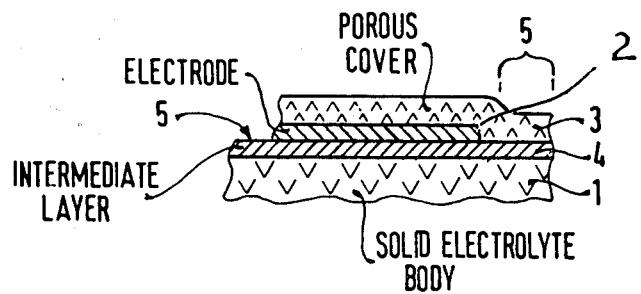

FIG. 1 illustrates, highly schematically, a cross section through a portion of a solid electrolyte body in accordance with the prior art; and FIG. 2 illustrates a similar cross section with the intermediate layer in accordance with the present invention.

The solid electrolyte body 1 has an electrode layer 2, which may be a composite layer applied thereto, over which a porous cover layer 3 can be applied, although the cover layer 3 is not necessary. In accordance with the present invention, an additional or intermediate layer 4 is placed between the solid electrolyte body and the electrode layer 2. The electrode layer 2, itself, can be a composite layer system.

The formation of a three-phase boundary at the boundary surface between the solid electrolyte and the electrodes is limited in area, since the electron conductive components of the electrodes frequently have direct contact with non-conductive ion components of the solid electrolyte body. In accordance with the present invention, the introduction of the intermediate layer between the solid electrolyte body and the electrode can practically entirely eliminate the undesirable effect of the reduction of the formation of a three-phase boundary since the intermediate layer has a high ion conductivity. It is thus possible to utilize as the intermediate layer also expensive materials such as $Yb_2O_3$, since the quantity needed is very small.

The intermediate layer 4 in accordance with the present invention is desirable not only with electrode materials such as platinum, which is usually used, but also with oxide-type electrodes, in which the same conditions pertain as discussed above. For example, the intermediate layer can be made of fully stabilized zirconium dioxide, which can be used with perovskite electrodes such as doped $LaCoO_3$, and sintering the electrodes on the solid electrolyte body in porous form, which results in good adhesion. The operability of these electrodes is further improved if, thereafter, a coating of titanium dioxide or a titanium dioxide-aluminum oxide mixture, or aluminum oxide is applied thereover. The final sintering of the perovskite electrode layer is preferably carried out only after the cover layer of titanium dioxide, aluminum oxide or a titanium dioxide-aluminum oxide mixture has been applied.

The formation of the fully stabilized intermediate layer applied to a partially stabilized $ZrO_2$ ceramic has the additional advantage that damages to the structure due to irreversible changes of metastable tetragonal $ZrO_2$ are less likely to occur. Such structural damages could occur first on the surfaces of a densely sintered partially stabilized ceramic, from where they will penetrate from the outer surface towards the interior of the ceramic. The intermediate layer, in accordance with the invention, prevents the transformation or conversion of the metastable tetragonal phase due to the fully stabilized zirconium dioxide surface layer, since the monoclinic $ZrO_2$, due its higher lattice volume, can occur only if the space necessary therefor is available, for example at the surface, or the space can be generated due to occurrence of fissures or extension of fissures. Therefore, it is preferred to cover the entire surface of the solid electrolyte body with the intermediate layer 4 also in those regions where an electrode layer is not necessarily applied, that is, even if the electrode layer 2 is applied later on only on a portion of the layer 4 in order to protect the solid electrolyte body 1, if it is only partially stabilized, against damage to its microstructure.

If the electrode layer consists only of a track of conductive material, so that the major portion of the solid electrolyte surface is not covered by the electrode, then the remaining surface of the electrode can be covered with a surface coating layer of fully stabilized zirconium dioxide. This surface coating layer may contain up to 85% (by volume) of $Al_2O_3$, preferably from between 15 to 50% (by volume). The surface zone thus will have a high mechanical strength since grain growth is substantially limited upon the sintering processes which are carried out after application of the surface layer.

Various methods to make the solid electrolyte body with the layer applied thereto, particularly for electrochemical automotive-type sensors, are possible. In accordance with a feature of the invention, the intermediate layer 4 can be applied to a partially stabilized zirconium dioxide body 1 by applying a thin layer of stabilizer oxide thereon. The thus applied stabilizer oxide then diffuses upon a sintering process or upon a thermal treatment of the solid electrolyte body into the body itself. This process can be accelerated by pretreatment of the surface of the solid electrolyte body 1, for example by etching, sandblasting, or the like. The layer 4 will then be in form of a diffusion zone.

Other processes are suitable; for example, a thin layer of stabilizer oxide can be applied by spraying a suspension of oxide on the surface; or a suspension or solution being applied is arranged to contain a compound which contains the stabilizer cation in a form such that it can be thermally decomposed or that it can be oxidized. Raw materials which are suitable are, for example, compounds such as carbonates, acetates, or the like.

Another way of application is to dip the sensor area which is to be covered into such a suspension or solution, or to pour the suspension or solution over the solid electrolyte body 1.

Coating can also be effected by vapor deposition, sputtering, or similar processes. Layers which can be oxidized are then generated, such as metallic yttrium or ytterbium or, respectively, yttrium-zirconium or ytterbium-zirconium layers. The corresponding oxides may also be reactively precipitated. These respective processes are only advantageous, however, if the applied layer should have a particularly high degree of uniformity.

The solid electrolyte body is useful and particularly advantageous not only in the field of lambda sensors, for use in determining the exhaust gas composition from internal combustion engines and particularly automotive-type internal combustion engines; rather, the thus coated solid electrolyte, and the method of application, is also suitable for use with polarographic or limit current sensors, that is, sensors which operate in the region of the diffusion limit current. The solid electrolyte body with the layer 4 thereon can be used to obtain better limit current relationships, that is, more desirable limit current curves suitable for operation at lower operating temperatures.

DESCRIPTION OF AN EXAMPLE

The invention will be described in connection with a lambda sensor which has the shape of a tube, closed at one end, as well known, for example of the type described in U.S. Pat. No. 3,978,006, Topp et al, assigned to the assignee of the present application. The solid electrolyte tube is made in well known manner of a zirconium oxide ceramic which is fully or partially stabilized with yttrium oxide, and presintered for 2 hours at 1050° C. This presintered tube is then coated with the coating 4 by a suspension of powder consisting of fully stabilized zirconium dioxide in water, by dipping and subsequent throwing off or spinning off or, alternatively, by spraying the powder-aqueous suspension thereon. The powder in the suspension contains 92 mol-% $ZrO_2$ 8 mol-% $Y_2O_3$ or 8 mol-% $Yb_2O_3$.

This powder preferably may contain up to 3% (by weight) sinter-active $Al_2O_3$ in order to improve the sintering activity of the layer. The coating is dried and then heated for 2 hours at 1000° C. to provide an intermediate incandescent step. The outer surface which faces the exhaust gases, as well as the inner surface of the closed tube which faces the reference gas—typically ambient air—have platinum-cermet electrodes applied thereto by spraying-on or brushing-on. These platinum-cermet electrodes are made of 60 parts (by volume) platinum powder and 40 parts (by volume) of fine, stabilized zirconium dioxide powder. The solid electrolyte tube with the electrodes thus applied is then sintered. A fully stabilized solid electrolyte ceramic is sintered at 1500° to 1650° C.; a partially stabilized ceramic at 1400° to 1600° C. Subsequent to the sintering, it is desirable to apply at least on the electrode which is exposed to exhaust gases a porous ceramic cover layer 3, for example made of magnesium spinel, in well known manner. The inner zone or layer 4 can be applied by filling the presintered tube with the suspension and then pouring it out, leaving a residue coating. The suspension may also contain $Sc_2O_3$ or other oxides of heavy rear earths.

The intermediate layer of fully stabilized zirconium dioxide can have a multi-layer system applied thereto, as described in German Disclosure Document DE-OS No. 28 52 647, to which U.S. patent application Ser. No. 098,602, filed Nov. 29, 1979 and now U.S. Pat. No. 4,296,148, by the inventor hereof, "Method to Apply Multiple Layers, Including an Electrode Layer, on a Sintered or Presintered Ion-Conductive Solid Electrolyte Body", and assigned to the assignee of this application, corresponds. The platinum-cermet electrodes are applied in the above-described manner; the solid electrolyte tube, with the electrodes applied, is not fully sintered, however, but rather is dried for 2 hours at about 900° C., or preheated to incandescence, respectively. The two electrodes are then coated with an aqueous aluminum oxide slip which, for example, contains ground sinter-active alumina and in addition a small portion of a binder, for example about 2% (by weight—with reference to the solid material content) of polyvinylalcohol. With respect to the outer electrode, the application can be by spraying-on, dipping into the slip, or the like; for the inner electrode, the slip is preferably sprayed in or the slip is filled into the inner opening of the hollow solid electrolyte tube, and thereafter poured out, leaving a film-like residue. After drying of the slip, the solid electrolyte with the intermediate layer and this combined layer is sintered as above described, that is, fully stabilized solid electrolyte ceramic at 1500° to 1650° C., whereas partially stabilized ceramics are sintered at 1400° to 1600° C.

If the starting material of the body 1 is a partially stabilized solid electrolyte body, then the intermediate layer 4, of fully stabilized zirconium dioxide, can be generated by applying to the solid electrolyte body a pure stabilizer oxide in a thickness of from about 0.2 to 2 $\mu m$ (and forming the preferred range) and, at a thermal treatment of above 1400° C., diffusing the stabilizer oxide into the adjacent layer of the solid electrolyte body to form fully stabilized zirconium dioxide. Rather than using a stabilizer oxide, a thermally decomposable compound such as a carbonate or acetate of yttrium or ytterbium, or metals themselves may be applied to the solid electrolyte surface which, in a subsequent thermal treatment at above 1200° C. is transformed into corresponding oxides and which, again, diffuse into the adjacent zone of the solid electrolyte to form fully stabilized zirconium dioxide. The oxides or the compounds which can dissociate are applied, for example, by spraying on, dipping, or pouring suspensions or solutions thereover; the metals are applied by vapor deposition or sputtering. Oxides can also be applied by reactive vapor deposition. The electrode layer or a composite electrode system consisting of a plurality of layers can be applied in a manner similar to that described above.

The intermediate zone 4 improves the current loading of the electrode and thus improves the start-up response of the electrochemical system which includes the solid electrolyte body so that it will become adequately operative already at temperatures in the order of about 300° C. The intermediate zone 4 can be zirconium dioxide which is fully stabilized with yttrium oxide or ytterbium oxide and, in a partially stabilized solid electrolyte ceramic body 1, additionally prevents defects in the structure due to thermal loading, particularly upon changeable thermal loading. The layer 4, thus, can be applied on the stabilized ceramic also in locations where the solid electrolyte body does not carry an electrode layer, that is, in the region 5 (FIG. 2). The intermediate layer 4 can be easily applied, requiring but few additional manufacturing steps.

Various changes and modifications may be made, and features described in connection with any one of the embodiments may be used with any of the others, within the scope of the inventive concept.

I claim:

1. Solid electrolyte sensor element for electrochemical sensing of composition of a gas to which the element is exposed comprising
   an electrode (2) positioned to contact said gas;
   an oxygen ion conductive solid electrolyte body (1) which comprises partially stabilized $ZrO_2$; and
   an ion conductive solid electrolyte intermediate layer (4) having a higher specific oxygen ion conductivity than said solid electrolyte body (1) and which does not contain metal and which consists essentially of fully stabilized $ZrO_2$ which is stabilized with a stabilizer oxide comprising at least one of the materials of the group consisting of $Y_2O_3$, $Yb_2O_3$, $Sc_2O_3$, oxides of heavy rare earth other than the foregoing, CaO and MgO,
   said intermediate layer (4) being located between and integral with the electrode (2) and the surface of the solid electrolytic body (1) thereby positioning the electrode (2) out of direct contact with the solid electrolyte body (1) to form the three phase boundary of said sensor element between (i) ion conductive solid electrolyte, (ii) electrode, and (iii) gas, at the contact of said electrode (2) and said ion conductive solid electrolyte intermediate layer (4).

2. Element according to claim 1, wherein the electrode (2) comprises a single electrode layer.

3. Element according to claim 1, wherein the electrode (2) comprises a composite electrode layer system.

4. Element according to claim 1, wherein the intermediate layer (4) and the solid electrolyte body (1) contain at least one of the materials: $Al_2O_3$; monoclinic $ZrO_2$;

and wherein the amount of said materials in the intermediate layer (4) is less than in the solid electrolyte body (1).

5. Element according to claim 4, wherein the intermediate layer is in the zone free from the electrode and comprises fully stabilized $ZrO_2$ which contains from between 2 to 85% (by volume) $Al_2O_3$, and which is fully stabilized with at least one of the materials of the group consisting of $Y_2O_3$, $Yb_2O_3$.

6. Element according to claim 5, wherein the $Al_2O_3$ content is between 15 to 50% (by volume).

7. Element according to claim 1, wherein the layer (4) extends over the surface of the sensor body (5) beyond the region or zone of application of the electrode (2).

8. In combination, an internal combustion engine and a solid electrolyte sensor element for electrochemical sensing of the composition of exhaust gases from the internal combustion engine, having a sensor comprising an oxygen ion conductive solid electrolyte body (1) and an electrode (2) on the surface of the body, and a surface layer (4) which consists essentially of an ion conductive solid electrolyte having a higher specific oxygen ion conductivity than the solid electrolyte body (1) and which does not contain metal, located between and integral with the electrode (2) and the surface of the solid electrolyte body (1) thereby positioning the electrode (2) out of direct contact with the solid electrolyte body (1) to form the three phase boundary of said sensor element between ion conductive solid electrolyte, electrode, and gases at the contact of said ion conductive solid electrolyte surface layer (4) and said electrode (2).

9. The combination according to claim 8, wherein the solid electrolyte body (1) comprises fully stabilized $ZrO_2$ and from 5 to 85% (by volume) $Al_2O_3$, and the layer (4) also comprises fully stabilized $ZrO_2$ containing less $Al_2O_3$ than said body (1).

10. The combination according to claim 9, wherein the content of $Al_2O_3$ of said body (1) is between about 5 to 50% by volume.

11. The combination according to claim 8, wherein the solid electrolyte body comprises partially stabilized $ZrO_2$;

and said surface layer (4) comprises fully stabilized $ZrO_2$ which is stabilized by at least one of the stabilizer oxides of the group consisting of CaO, $Y_2O_3$, $Yb_2O_3$, and MgO.

12. The combination according to claim 8, wherein said surface layer is fully stabilized $ZrO_2$, and is stabilized by at least one of the stabilizer oxides of the group consisting of $Y_2O_3$, $Yb_2O_3$, $Sc_2O_3$, or oxides of heavy rare earth other than the foregoing.

13. The combination according to claim 8, wherein said surface layer (4) and said solid electrolyte body (1) contain at least one of the materials: $Al_2O_3$; monoclinic $ZrO_2$;

and wherein the amount of said materials in said layer (4) is less than in the solid electrolyte body (1).

14. The combination according to claim 8, wherein the solid electrolyte body (1) comprises partially stabilized $ZrO_2$;

and said surface layer (4) in the area free from the electrode comprises fully stabilized $ZrO_2$ which contains from between 2 to 85% (by volume) $Al_2O_3$, and which is fully stabilized with at least one of the materials of the group consisting of $Y_2O_3$ and $Yb_2O_3$.

15. The combination according to claim 14, wherein the $Al_2O_3$ content is between 15 to 50% (by volume).

* * * * *